United States Patent
Kobold et al.

(10) Patent No.: US 7,951,598 B2
(45) Date of Patent: May 31, 2011

(54) DIFFERENTIAL HEMOLYSIS OF A WHOLE BLOOD SAMPLE

(75) Inventors: Uwe Kobold, Weilheim (DE); Thomas Duelffer, Weilheim (DE); Rupert Herrmann, Weilheim (DE); Herbert von der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/328,890

(22) Filed: Dec. 5, 2008

(65) Prior Publication Data

US 2009/0253210 A1 Oct. 8, 2009

Related U.S. Application Data

(63) Continuation of application No. PCT/EP2007/004923, filed on Jun. 4, 2007.

(30) Foreign Application Priority Data

Jun. 6, 2006 (EP) ..................................... 06011604

(51) Int. Cl.
G01N 33/48 (2006.01)

(52) U.S. Cl. .......... 436/63; 436/161; 436/173; 436/174; 210/656; 250/282

(58) Field of Classification Search .................... 436/63, 436/161, 173, 174, 175, 177, 178; 435/2; 422/70, 101, 527, 535; 210/656, 198.2; 250/282
See application file for complete search history.

(56) References Cited

U.S. PATENT DOCUMENTS

| | | | |
|---|---|---|---|
| 4,056,468 A | 11/1977 | Breiter et al. | |
| 4,286,963 A | 9/1981 | Ledis et al. | |
| 4,529,705 A | 7/1985 | Larsen | |
| 5,292,663 A | 3/1994 | Yamazaki et al. | |
| 5,316,951 A | 5/1994 | Carver, Jr. et al. | |
| 5,874,310 A | 2/1999 | Li et al. | |
| 5,882,934 A | 3/1999 | Li et al. | |
| 6,043,032 A * | 3/2000 | Yamagishi | 435/6 |
| 6,050,956 A | 4/2000 | Ikegami et al. | |
| 6,322,695 B1 | 11/2001 | Lee et al. | |
| 6,428,704 B1 * | 8/2002 | Setoguchi et al. | 210/635 |
| 6,451,609 B1 | 9/2002 | Xu et al. | |
| 6,723,236 B2 | 4/2004 | Fisk et al. | |
| 6,864,100 B1 | 3/2005 | Ribbe et al. | |

FOREIGN PATENT DOCUMENTS

| | | |
|---|---|---|
| EP | 0185048 B1 | 6/1986 |
| EP | 0185170 A2 | 7/1986 |
| EP | 0305491 B1 | 3/1989 |
| EP | 0794435 B1 | 9/1997 |
| EP | 0874988 | 11/1998 |
| EP | 1000356 B1 | 5/2000 |
| EP | 1103812 A1 | 5/2001 |
| JP | 2000081424 A1 | 3/2001 |
| WO | 9967647 A1 | 12/1999 |
| WO | 02101087 A1 | 12/2002 |

OTHER PUBLICATIONS

Boyer, S. et al., "Enrichment of Erythrocytes of Fetal Origin From Adult-Fetal Blood Mixtures via Selective Hemolyis of Adult Blood Cells: An Aid to Antenatal Diagnostics of Hemoglobinopathies," Blood 47:6 (Jun. 1976) 883-897.
Fazili, Z. et al., "Erythrocyte Folate Extraction and Quantitative Determination by Liquid Chromatography-Tandem Mass Spectrometry: Comparison of Results with Microbiologic Assay," Clinical Chemistry 51:12 (2005) 2318-2325.
Gunter, E. et al., "Results of an international round robin for serum and whole-blood folate," Clinical Chemistry 42:10 (1996) 1689-1694.
Jones, K. et al., "An Immunoassay for the Measurement of Sirolimus," Clinical Therapeutics 22: Suppl B (2000) B49-B61.
Koal, T. et al., "Simultaneous determination of four immunosuppressants by means of high speed and robust on-line solid phase extraction-high performance liquid chromatography-tandem mass spectrometry," Journal of Chromatography B 805 (2004) 215-222.
Murthy, J. et al., "Tacrolimus Metabolite Cross-Reactivity in Different Tacrolimus Assays," Clinical Biochemistry 31:8 (1998) 613-617.
Pfeiffer, C. et al., "Determination of Folate Vitamers in Human Serum by Stable-Isotope-Dilution Tandem Mass Spectrometry and Comparison with Radioassay and Microbiologic Assay," Clinical Chemistry 50:2 (2004) 423-432.
Sarapuk, J. et al., "Influence of Counterions on the Interaction of Pyridinium Salts with Model Membranes," Z. Naturforschung 54c (1999)952-955. Yang, Z. et al., "Immunosuppressants" Pharmacokinetics, methods of monitoring and role of high performance liquid chromatography/mass spectrometry, Clinical and Applied Immunology Reviews 5 (2005) 405-430.
"Therapeutic drug monitoring—is it important for newer immunosuppressive agents?" Durg Ther Persp 17:22 (2001) 8-12.
Greiling, H. and Gressner, A. M., Lehrbuch der Klinischen Chemie und Pathobiochemie, 3rd Edition, 1995, pp. 460-462, Schattauer, Stuttgart-New York.

* cited by examiner

*Primary Examiner* — Maureen M Wallenhorst (57) ABSTRACT

The invention relates to a method for differentially hemolyzing whole blood. It discloses methods for detecting an analyte in a liquid sample known or suspected to contain red blood cells and suspected or known to contain eukaryotic cells, the method including the steps of processing the liquid sample with a membrane solubilizing agent under conditions appropriate to lyse cell membranes of red blood cells and at the same time not to cause precipitation of sample constituents, subjecting the processed sample to a chromatographic separation, and detecting the analyte. The differential hemolysis of red blood cells is of advantage in a method of detecting an analyte in a liquid sample that may contain both erythrocytes and nucleated cells. The differential solubilization of red blood cells can be easily combined with an online detection methodology, like LC-MS, and is advantageous in the detection of many analytes, e.g. in the detection of folate or of immunosuppressive drugs, like tacrolimus or sirolimus.

7 Claims, 5 Drawing Sheets

DIFFERENTIAL HEMOLYSIS OF A WHOLE BLOOD SAMPLE

RELATED APPLICATIONS

This application is a continuation of International application PCT/EP2007/004923 filed Jun. 4, 2007 which claims priority to European application EP 06011604.3 filed Jun. 6, 2006.

FIELD OF THE INVENTION

The present invention relates to a method of detecting an analyte in a liquid sample known or suspected to comprise red blood cells and suspected or known to comprise eukaryotic cells, the method comprising the steps of processing said liquid sample with a membrane solubilizing agent under conditions appropriate to lyse cell membranes of red blood cells and at the same time not to cause precipitation of sample constituents, subjecting the processed sample to a chromatographic separation, and detecting the analyte. The differential hemolysis of red blood cells is of advantage in a method of detecting an analyte in a liquid sample that may comprise both erythrocytes as well as nucleated cells. The differential solubilization of red blood cells can be easily combined with an online detection methodology, like LC-MS, and is advantageous in the detection of many analytes, e.g. in the detection of folate or of immunosuppressive drugs, like tacrolimus or sirolimus.

BACKGROUND OF THE INVENTION

The more constituents are present in a sample the more difficult is the analysis of a target analyte comprised therein. Red blood cells contain a dramatic amount of proteins and small molecular weight constituents that potentially interfere with an analyte to be detected from a biological fluid like whole blood. This is one of the major reasons why in clinical routine preferably blood plasma (often simply referred to as plasma, i.e. an anticoagulated whole blood sample; deprived of cells and erythrocytes) or blood serum (often simply referred to as serum, i.e. coagulated whole blood; deprived of cells, erythrocytes and most proteins of the coagulation system, especially of fibrin/fibrinogen), respectively, are used. Whole blood samples also tend to be more difficult to handle, e.g., as compared to serum or plasma. Whole blood tends to be less stable and slow rupture of erythrocytes impairs a reliable measurement of quite a few analytes of interest.

In addition, at this point in time it does not appear to be feasible to use a whole blood sample in many of the existing online detection methods. It is for example not possible to use a whole blood sample in a clinical diagnostic routine procedure requiring a separation step based on liquid chromatography (LC).

Routine liquid chromatographic separation usually is based on a column essentially consisting of a filter unit or frit to protect the column material and the column material required for the separation of the analyte(s) of interest. If whole blood is applied to such column, the column will be blocked rather soon or even immediately, depending on column size and system. This problem makes it merely impossible to use whole blood in an online detection process in combination with an LC-method as for example preferred in clinical routine diagnosis. At present it appears that appropriate separation/handling of a blood sample, e.g. by centrifugation, filtration, precipitation or analyte extraction is essential, before such processed sample can be properly and reliably analyzed.

As indicated above, serum or plasma may be obtained from whole blood and used in the detection of an analyte. Cells and erythrocytes in theory may also be removed by filtration or centrifugation from whole blood. However, these methods are neither appropriate for use in a routine diagnostic setting, nor would they allow for a correct measurement of those analytes at least partially present inside red blood cells.

In a further way of sample processing the analyte of interest is first separated from the majority of potentially interfering substances by selective precipitation or extraction methods. Extraction can be performed in liquid phase or on a solid phase. This shall be exemplified by illustrating some of the procedures used in the detection of immunosuppressive drugs.

Well-known immunosuppressive drugs are e.g. mycophenolate mofetil (MMF), rapamycin (RAPA also known as sirolimus) and tacrolimus (FK-506). Therapeutic drug monitoring for immunosuppressive drugs is especially important for transplant patients as well as for patients suffering from AIDS (cf e.g.: Drug Ther. Perspect. 17 (22) (2001) 8-12). Most patients who undergo solid organ transplantation require lifelong immunosuppressive therapy to prevent allograft rejection. But, because many immunosuppressive agents have narrow therapeutic ranges, and are associated with various toxicities and the potential for drug interactions, the use of therapeutic drug monitoring (TDM) in conjunction with clinical assessment of patients may be particularly important.

Mycophenolate mofetil is a prodrug. After oral administration, mycophenolate mofetil (MMF) undergoes rapid hydrolysis in the intestine and blood to form its active metabolite mycophenolic acid (MPA). MMF is widely available and is approved in the US and UK for the prevention of renal, hepatic or cardiac allograft rejection in combination with corticosteroids and cyclosporin. The drug has demonstrated superiority over azathioprine in reducing the incidence of acute rejection of renal allografts. The therapeutic trough concentration is in the range of 1-3.5 mg/L. MMF can be measured from plasma and from whole blood.

Tacrolimus is a macrolide antibiotic that was first approved by the US Food and Drug Administration (FDA) in 1994 for the prevention of liver allograft rejection. It is up to 100 times more potent than cyclosporin in vitro, and clinically, it is associated with a greater reduction in the incidence of tissue rejection. Tacrolimus has demonstrated efficacy both as primary immunosuppressive therapy in patients undergoing various transplantation procedures and as rescue therapy for patients with refractory acute allograft rejection after liver or kidney transplantation. The therapeutic trough concentration is in the range of 5-20 µg/L.

Since at least part of the tacrolimus present in the circulation is compartmented within erythrocytes, a whole blood sample is used in the clinical routine measurement of this drug. Tacrolimus can e.g. be detected by high performance liquid chromatography (HPLC), HPLC mass spectrometry (MS), radio receptor assay (RRA), or by an immunoassay (IA). The latter two methodologies do not detect tacrolimus and certain of its various metabolites with the same sensitivity. This may lead to an interference in the procedure used (Murthy, J. N., et al., Clin. Biochem. 31 (1998) 613-617). At least in the detection of the various tacrolimus metabolites the HPLC-MS-procedure may be considered the gold standard. All the procedures mentioned above, however, require the extraction of tacrolimus from whole blood. Usually acetonitrile is used in clinical routine for the extraction of tacrolimus from whole blood and no method appears to exist that would allow for an online measurement of tacrolimus from a whole blood sample.

Sirolimus is, like tacrolimus, a macrolide antibiotic. It was first approved in 1999 by the US FDA for the prevention of allograft rejection after kidney transplantation, and indeed has shown promising results in this respect when used acutely in combination with cyclosporin and corticosteroids. In vitro, sirolimus is up to 100 times more potent than cyclosporin, and clinically, it may exhibit synergism with cyclosporin, perhaps permitting a reduction in cyclosporin dosage. The therapeutic trough concentration is in the range of 5-15 µg/L.

As for tacrolimus, a significant amount of sirolimus is present within erythrocytes. Therefore extraction of a whole blood sample is required no matter which detection method is used. In clinical routine a sample suspected to comprise sirolimus is subjected to HPLC and sirolimus is detected by ultraviolet light (UV) or by MS/MS. Recently also a microparticle enzyme immunoassay has been described (Jones, K., et al., Clinical Therapeutics 22, Suppl. B (2000) B49-B61).

Folate is the collective name of a group of related molecules differing in oxidation state. Folates are part of the water-soluble vitamin B group and are important as coenzymes for homocysteine metabolism and in the transfer of one-carbon groups required for DNA replication. Inadequate folate status is related to increased risk of neural tube defects, is associated with cardiovascular disease, anemia, with certain cancers and with Alzheimer's disease. Serum or plasma folate concentrations reflect recent dietary intake, whereas erythrocyte folate concentrations are more indicative of body stores (Gunter, E. W. et al., Clin. Chem. 42 (1996) 1689-1694; Fazili, Z. et al., Clin. Chem. 51 (2005) 2318-2325; Pfeiffer, C. M., et al., Clin. Chem. 50 (2004) 423-432). Erythrocyte total folate (red blood cell folate=RBC-folate) is the best measure of whole body folate status. Recent studies have shown that 5-methyl tetrahydrofolate is the dominant folate vitamer in circulating erythrocytes. For the diagnosis of folate deficiency it is recommended that determinations are performed not only from serum or from plasma but also from erythrocytes, since folate is localized to more than 95% in the latter. The concentration in the erythrocytes more truly reflects the actual folate status.

A number of methods are available to measure folate in different matrices. The major analytical methods are microbiological assay, radio immuno assay, chemiluminescence, chromatographic methods and mass spectrometric methods. Most methods are based on competitive binding of folate to folate binding protein.

For the measurement of RBC-folate the use of a hemolyzing reagent is obviously mandatory. For example the ELECSYS assay (Roche Diagnostics GmbH) for determination of RBC folate uses ascorbic acid as lysis reagent. ELECSYS RBC-folate hemolyzing reagent is used together with the ELECSYS folate assay for the quantitative determination of folate in erythrocytes (RBC-folate). Whole blood treated with anticoagulants (heparin or EDTA) is diluted with ascorbic acid solution (0.2%) and incubated for approximately 90 minutes at 20-25° C. Lysis of the erythrocytes takes place, with liberation of the intracellular folate. The hemolysate is then used as a "prediluted" sample (in analogy to serum) for subsequent measurement in the ELECSYS folate assay. The hematocrit value determined in whole blood and the dilution effect brought about by pretreatment of the sample is compensated for in the calculation of the erythrocyte folate concentration (Greiling, H., Gressner, A. M., Lehrbuch der Klinischen Chemie und Pathobiochemie, 3rd ed., Stuttgart-New York, Schattauer (1995) pp. 460-462; Gunter, F. W., et al., Clin. Chem. 42 (1996) 1689-1694).

The hemolysate generated by treatment with ascorbic acid can not be used for routine chromatographic procedures. For use of such hemolysate in a chromatographic procedure, or mass spectrometric determination it is necessary to remove cell debris and precipitated protein prior to analysis.

Debris and precipitated proteins usually are removed from a sample by centrifugation, offline filtration or solid phase extraction.

Solid phase extraction (SPE) is a chromatographic technique which is widely used, e.g., for preconcentration and cleanup of analytical samples, for purification of various chemicals, and for removal of toxic or valuable substances from aqueous solutions. SPE is usually performed using a column or cartridge containing an appropriate resin. SPE procedures have been developed using sorbents which can interact with analytes by hydrophobic, ion exchange, chelation, sorption, and other mechanisms, to bind and remove the analytes from fluids. Since different SPE applications for different classes of analytes can require different sorbents, there is a concomitant need for sorbents with specific properties which have unique selectivity for the analyte or class of analytes of interest. Representative examples of SPE materials and SPE columns, respectively, can be found in U.S. Pat. No. 6,322,695 and U.S. Pat. No. 6,723,236.

The concentration of hemoglobin itself as well as the ratio of glycated hemoglobin (HbA1c) to non-glycated hemoglobin are important analytes in hematology and diabetes. In such assessment the erythrocytes comprised in a whole blood sample are lysed and the hemoglobin is then measured. U.S. Pat. No. 6,050,956 describes a hemolyzing tube that is prefilled with a standardized amount of a blood dissolving liquid. However, whole blood is first collected into a routine blood collection tube. Thereafter blood is diluted 1 plus 100 into the hemolyzing tube. Due to the very high concentration of hemoglobin a 1 plus 100 dilution of whole blood is possible and no differential hemolysis, i.e. no hemolysis avoiding negative side effects like protein precipitation and/or release of DNA, is required. Usually HbA1c is then detected by an immunoassay.

Various patent families to Coulter International Inc., like U.S. Pat. No. 5,874,310; U.S. Pat. No. 5,882,934; EP 1 000 356; EP 0 874 988; EP 0 305 491 or EP 0 185 048 relate to the field of hematology and especially to the analysis of blood cells. In EP 0 794 435 the use of N-monoalkylated pyridinium salts having an alkyl chain from eight to twenty C-atoms in the analysis of the eukaryotic cells as comprised in a blood sample is disclosed. U.S. Pat. No. 5,316,951 mentions that N-monoalkylated pyridinium salts having an alkyl chain from ten to twenty C-atoms may be used in the analysis of the eukaryotic cells as comprised in a whole blood sample.

Sarapuk, J. et al., Z. Naturforschung 54c (1999) 952-955, mention that 3-Carbamoyl-1-decyloxymethyl pyridinium chloride may be used to lyse red blood cells.

EP 1000 356 e.g. describes an improved diluent for dilution of a blood sample that is suited for enumeration and sizing of blood cells, determination of hemoglobin parameters and differentiation of leukocyte sub-populations in a single blood sample. Analysis is performed by use of suitable electronic instrumentation. For such analysis blood is usually collected by a physician, then has to be transported to the clinical laboratory, and only shortly before analysis a lysis reagent is added.

The references available to the inventors of the present invention neither disclose nor suggest that a hemolyzed whole blood sample could be used in the online separation by an liquid chromatographic method, e.g., in the detection of an analyte usually present in a red blood cell.

Alike to quite a few other analytes of interest, there appears to be no method available that would allow for the detection of folate, sirolimus or tacrolimus from a whole blood sample in any detection method based on the use of an online chromatographic procedure.

It becomes obvious from the above discussion of the state of the art that no method for an online chromatographic separation and measurement of an analyte from a whole blood sample appears to be available. All routine procedures even today appear to require the extraction or fractionation of an analyte of interest or of a certain class of compounds comprising the analyte of interest from the rest of such sample.

It would, however, be highly desirable if whole blood could be used directly as a sample. This would be especially advantageous in an online detection procedure making use of a liquid chromatography (LC) separation step. It is also obvious that the direct online detection of an immunosuppressive drug from whole blood would be an important progress for a clinical routine laboratory.

It has now surprisingly been found and could be established that it is possible to process a sample of whole blood by aid of a suitable membrane solubilizing agent, to e.g. render it an appropriate sample for direct separation by LC and analyte detection by MS. It has also been possible to detect an analyte in such processed sample. This is especially valuable for an analyte that is also present to a relevant extend inside red blood cells, like the immunosuppressive drugs sirolimus and tacrolimus or like folate.

SUMMARY OF THE INVENTION

In a first embodiment the present invention relates to a method of detecting an analyte in a liquid sample known or suspected to comprise red blood cells and suspected or known to comprise eukaryotic cells, the method comprising the steps of processing said liquid sample with a membrane solubilizing agent under conditions appropriate to lyse cell membranes of red blood cells and at the same time not causing precipitation of sample constituents, subjecting the processed sample obtained in the first step to a chromatographic separation, and detecting the analyte.

In a further preferred embodiment the present invention relates to the use of a membrane solubilizing agent in the processing of a whole blood sample for liquid chromatography and to the use of a processed blood sample obtained by differential hemolysis with a membrane solubilizing agent according to the present invention in a liquid chromatography-based analysis.

DETAILED DESCRIPTION OF THE INVENTION

The method according to the present invention is performed in vitro, i.e. not on the human or animal body.

In a preferred embodiment the present invention relates to a method of detecting an analyte in a liquid sample known or suspected to comprise red blood cells and suspected or known to comprise eukaryotic cells, the method comprising the steps of a) processing said liquid sample with a membrane solubilizing agent under conditions appropriate to lyse cell membranes of red blood cells and at the same time not causing precipitation of sample constituents, b) subjecting the processed sample obtained in step (a) to a chromatographic separation, and c) detecting the analyte.

"Red blood cells" in the sense of the present invention are red blood cells not having a cell nucleus. Such red blood cells not having a cell nucleus are e.g. the mature red blood cells as found in the circulation of mammals. This invention does not relate to nucleated red blood cells as e.g. known from avian species. The later ones would meet the criteria for nucleated or eukaryotic cell.

"Mammal" for purpose of the present invention refers to any animal classified as a mammal, including humans, domestic and farm animals, and zoo, sports, or pet animals, such as dogs, cats, cattle, horses, sheep, pigs, goats, rabbits, etc. Preferably, the mammal is human.

A "eukaryotic cell" or a "nucleated cell" in the sense of the present invention is a cell derived from a eukaryotic organism and is still having its cell nucleus. Examples of eukaryotic cells are cells derived from nucleated tissue, nucleated tissue culture cells and nucleated blood cells. In a preferred embodiment the eukaryotic cell is a nucleated blood cell like a thrombocyte, a monocyte, neutrophils, eosinophils or a leukocyte. Cells from lower organisms, like bacteria, though containing genetic material, are not eukaryotic cells.

The articles "a" and "an" are used herein to refer to one or to more than one (i.e. to at least one) of the grammatical object of the article. By way of example, "a red blood cell" means one red blood cell or more than one red blood cell.

The advantageous properties of differential hemolysis, i.e. of processing a liquid sample with a membrane solubilizing agent under conditions appropriate to lyse cell membranes of red blood cells and at the same time not to cause precipitation of sample constituents, as demonstrated in the present invention have been established by using whole blood samples. However, now that the method is established also other liquid samples may be used and processed the same way. Therefore, the liquid sample according to the present invention may be any sample as investigated in clinical diagnostic routine, like urine, cerebrospinal fluid, serum, plasma or blood.

Preferably the liquid sample subjected to a differential hemolysis with an appropriate membrane solubilizing agent comprises red blood cells and may comprise or comprises nucleated cells. Further preferred the liquid sample comprises both red blood cells and nucleated cells. Preferably the liquid sample according to the present invention will be whole blood. As will be appreciated a whole blood sample contains both red blood cells without nuclei as well as nucleated blood cells.

Preferably the whole blood sample is processed directly, i.e. directly after sampling in the method according to the present invention. Preferably the blood sample will be not treated at all before it is subjected to the differential hemolysis according to the present invention. Also preferred, the whole blood will be collected/treated with an appropriate anti-coagulant to yield an anti-coagulated whole blood sample, before it is differentially hemolyzed. Well-known anti-coagulants frequently used in clinical diagnostic routine are heparin, citrate and EDTA. Preferably the sample according to the present invention is an anti-coagulated whole blood sample, especially a citrated whole blood sample or an EDTA-anti-coagulated whole blood sample.

In a method according to the present invention the liquid sample is treated with the membrane solubilizing agent in such a manner that two requirements are met: a) if red blood cells are present, the membranes of red blood cells are disrupted and b) at the same time no precipitation of sample constituents is caused. This process is termed differential hemolysis. In case the method is practiced on a whole blood sample a processed sample is obtained containing lyzed red blood cells but at the same no precipitate.

Preferably the membrane solubilizing agent according to the present invention will bring about the lysis of at least 95% of the erythrocytes present in a sample. Further preferred the reagent for differential hemolysis will bring about the lysis of at least 97%, 98%, 99%, 99.5% of the erythrocytes present in a sample.

Without wanting to be bound to the following theory one may assume that the advantageous balance found and established within the framework of the present invention, at which the membrane of a red blood cell is disrupted but at which at the same time no precipitation of sample constituents is caused is essential for overcoming at least some of the problems known from the art. By applying a suitable membrane solubilizing agent under appropriate conditions the integrity of the cellular membrane that is e.g. essential for shielding the contents of a red blood cell from the blood plasma is lost. The content of the erythrocytes (e.g. hemoglobin but also some analytes of interest) is released into the surrounding liquid. At the same no precipitation of sample constituents is caused.

As the skilled artisan will appreciate, sample constituents that might interfere with a latter analysis may especially be DNA and de-natured proteins, respectively. As long as the nuclei of eukaryotic cells, e.g. like lymphocytes or monocytes are not destroyed, no DNA is released from these nuclei. As long as no proteins precipitate, proteins comprised in the sample subjected to differential hemolysis will not interfere, at least not to a significant extend, with the chromatography step or with the analysis.

The integrity of red blood cells can for example be easily assessed by appropriate life stains. In a preferred embodiment according to the present invention trypane blue is used in order to assess the integrity of a red blood cell, membrane. Intact red blood cells do not accumulate trypane blue, whereas a red blood cell with a disrupted membrane does stain with trypane blue. The membrane integrity of a red blood cell is easily assessed under the microscope after staining a sample with trypane blue. The percentage of disrupted red blood cells is calculated by counting intact red blood cells before and after the treatment, by then dividing the first number by the latter number and by then multiplying this value by 100. Red blood cells that are solubilized are referred to as lyzed red blood cells or as lyzed erythrocytes.

The appropriate treatment will be adequate to lyse a red blood cell, but at the same time it will not cause precipitation of sample constituents. It is expected that the appropriate hemolysis treatment in a method according to the present invention will also effects the outer membranes of eukaryotic cells. However, care can and must be taken that the DNA contained in the cell nuclei is not released into the sample. The hemolysis reagent and the conditions for hemolysis used will either and preferably leave the nuclear membrane and thus the nuclei macroscopically intact or at least DNA will not be set free from its surrounding and DNA-stabilizing nuclear proteins. If DNA would be released to a significant extend such DNA might or even would interfere with further handling of the sample. Released DNA e.g. tends to make the liquid very viscous. It is then no longer possible to pipette or transfer such sample or to pass it through certain filters or columns.

Care can and must also be taken that no protein precipitation occurs. As the skilled artisan will appreciate, there are many, many different proteins present in a biological sample, e.g. in a whole blood sample. All these proteins have individual properties influencing their tendency to precipitate or aggregate.

It has now been found that it is possible to describe and define whether sample processing with a membrane solubilizing agent is performed under appropriate conditions in order lyse cell membranes of red blood cells on the one hand and at the same time not to cause precipitation of sample constituents. Both, red blood cells not lysed as well as precipitated sample constituents have a negative impact on the properties of such sample.

Whether the conditions for differential hemolysis are appropriate can be easily and preferably determined by using the following standardized procedure. A whole blood sample with a hematocrit of 40 is diluted 1:10 and mixed 1:1 with the candidate hemolysis reagent. The efficacy of a reagent for bringing about differential hemolysis is seen visually. Upon lysis of the erythrocytes the mixture becomes clear. If precipitation of sample constituents occurs the sample becomes turbid or viscous or both.

As indicated above, the conditions used in a method of differential hemolysis according to the present invention can easily be assessed visually. If a whole blood sample is incubated with an appropriate candidate reagent for differential hemolysis the minimal concentration required to hemolyze red blood cells can be recognized as the concentration rendering the turbid blood sample transparent or clear. The highest possible concentration is the one still leading to a transparent and non-viscous sample.

It has turned out rather easy to determine the appropriate minimal final concentration of the candidate hemolysis reagent as the concentration leading to the change in transparency of a treated whole blood sample. This change in transparency correlates well with the suitability of such processed sample for direct analysis by HPLC. However, for the sake of an unambiguous definition it is preferred that minimal concentration of a hemolysis reagent is confirmed by the HPLC method as described below.

The maximal concentration of hemolysis reagent possible is the concentration still not causing release of DNA and/or precipitation of a protein. The sample thereby would turn viscous or turbid or both and is not suitable for a direct HPLC application anymore. Whereas viscosity and turbidity can be followed visually it is preferred that maximal concentration of a hemolysis reagent is confirmed by an HPLC method as described below.

Both, a whole blood sample still comprising too many non-lysed erythrocytes as well as a treated whole blood sample comprising precipitated sample constituents will not be suitable for any chromatographic procedure. This is why the conditions appropriate to bring about differential hemolysis preferably are determined by applying in a standardized manner a sample of whole blood treated with a candidate reagent for differential hemolysis to an HPLC column.

Incomplete hemolysis and/or precipitation of sample constituents is assessed by applying 50 times 10 µl of the processed whole blood sample to an HPLC column. To assess whether a candidate hemolysis reagent for differential hemolysis is appropriate, said hemolysis reagent is mixed with a sample of whole blood. Preferably EDTA-blood that has been prediluted 1:10 in physiological saline is used. It is mixed in a 1:1 ratio with the candidate hemolysis reagent and the mixture is incubated for 30 min at 20° C. The final dilution of whole blood in this mixture thus is 1:20. 50 aliquots of 10 µL of the this mixture, i.e. a processed whole blood sample are applied to a filter with a diameter of 2 mm and 0.5 µm pore size that is part of an HPLC system. In case the frit is part of an HPLC column the stationary phase must be selected not to cause any interference or blocking. The back-pressure is monitored. A candidate reagent for differential hemolysis that would cause an increase in back-pressure of 20 bar or more—if the back-pressure for injection 50 and the back-pressure for the first injection are compared to each other—would be deemed not to be appropriate. This way both the minimal as well as the maximal final concentration of an appropriate reagent for differential hemolysis can easily be identified. The minimal concentration is the lowest concentration of the candidate hemolysis reagent leading to differential hemolysis as assessed in the above described setting. The maximal concentration is the highest possible concentration of the candidate hemolysis reagent leading to a differential hemolysis but not causing precipitation of sample constituents as assessed in the above described setting.

Preferably the filter used in the above assessment of a candidate reagent for differential hemolysis is an HPLC frit. Also preferred the frit is part of an HPLC column of 20 mm in length filled with 3.5 µm Symmetry® C18 particles with a pore size of 100 A° as bed material, and having an inner column diameter of 2 mm.

As the skilled artisan will readily appreciate the whole blood sample used for such assessment is obtained from a healthy individual, i.e. an individual having no known disease and biochemical values in the normal range.

It has been found and established in the present invention that appropriate conditions can be established for quite many reagents in order to meet both the requirements for differential hemolysis.

The membrane solubilizing agent according to the present invention preferably is based on water as a solvent comprises a chemical or reagent bringing about the differential hemolysis as described above, and also preferred it may comprise a buffer and/or a preservative. The agents used for differential hemolysis preferably are based on chemicals or reagents with membrane solubilizing activity that have a molecular weight of less than 1000 Dalton.

The membrane solubilizing agent preferably is based on the membranolytic action, of one or more of the following chemicals: KBr; KJ; and KSCN or on a salt consisting of one or more of the following cations and anions.

The cation preferably is selected from wherein m is 0 or 1 and n is 4 or 6.

The anion is preferably selected from chloride, tetrafluoroborate, octylsulfate, iodide und thiocyanate. It is also possible to use mixtures of the above mentioned chemicals. As the skilled artisan appreciates it is these chemicals that facilitate the differential hemolysis whereas other ingredients of a hemolysis reagent may serve different purposes and may e.g. function as a buffer or as a preservative.

Preferably the chemical comprised in a reagent for differential hemolysis is a salt wherein the cation preferably is selected from wherein m is 0 or 1 and n is 4 or 6, and wherein the anion is preferably selected from chloride, tetrafluoroborate, octylsulfate, iodide und thiocyanate.

Appropriate membranolytic chemicals comprised in a membrane solubilizing agent are preferably selected from the group consisting of 1-Butyl-4-methylpyridinium tetrafluoroborate; 1-Butyl-3-methyl-imidazolium tetrafluoroborate; 1-Butyl-3-methyl-imidazoliumoctylsulfate; 1-Butyl-3-methyl pyridiniumchloride, 1-Hexylpyridiniumchloride; 1-Methyl-1-octyl pyrrolidiniumchloride; N-Octylpyridiniumchloride; 3-Carbamoyl-1-octyloxymethyl pyridiniumchloride; KBr; KJ; and KSCN, and of combinations thereof.

Preferably the membranolytic chemicals comprised in a membrane solubilizing agent are selected from the group consisting of 1-Butyl-4-methylpyridinium tetrafluoroborate; 1-Butyl-3-methyl-imidazolium tetrafluoroborate; 1-Butyl-3-methyl-imidazoliumoctylsulfate; 1-Butyl-3-methylpyridiniumchloride; 1-Hexylpyridiniumchloride; 1-Methyl-1-octyl pyrrolidiniumchloride; N-Octylpyridiniumchloride; and 3-Carbamoyl-1-octyloxymethyl pyridiniumchloride. It is further preferred to use a mixture of one these reagents and of KSCN.

As obvious to the skilled artisan, once an appropriate concentration of a candidate reagent for differential hemolysis has been identified in the above defined method that is based on a 1 in 20 dilution of a whole blood sample in a candidate hemolysis reagent, another ratio of whole blood sample to an adjusted hemolysis reagent can be used as required.

In case the analyte of interest is expected to be highly concentrated in the blood sample under investigation, the final concentration of the hemolysis reagent can stay the same as identified in the above setting and lower ratios of whole blood to hemolysis reagent, e.g., 1:30, 1:40 or 1:50 can be used. Preferably in a membrane solubilizing agent according to the present invention the reagent for differential hemolysis is used in at least the minimal concentration sufficient to achieve differential hemolysis as determined above.

In case the analyte of interest is present in rather a low concentration it may be necessary not to dilute the whole blood sample 1:20 but less. This is feasible by adjusting the concentration of the hemolysis reagent accordingly, such that the final relative concentration of hemolysis reagent to whole blood in the mixture of the hemolysis reagent and the whole blood sample stays within the ratio identified for the required minimal and maximal concentration, respectively, of hemolysis reagent as determined in the above described assessment.

By way of example: It has been found that 1-Methyl-1-octyl pyrrolidiniumchloride/KSCN if used in a final concentration of 1% and 0.4% in a membrane solubilizing agent according to the present invention, respectively, are appropriate to achieve the desired result, i.e. the differential hemolysis of a whole blood sample at a final dilution of 1:20. Dilution of an analyte in the processed blood sample can be reduced if for example the concentration of this hemolysis reagent is adjusted to 2% for 1-Methyl-1-octyl pyrrolidiniumchloride and 0.8% for KSCN, respectively. The membrane solubilizing agent comprising this adjusted concentration of hemolysis reagent, if later mixed 1:1 with a 1:5 diluted whole blood sample, also leads to differential hemolysis of the whole blood sample. Since the ratio of whole blood to hemolysis reagent is kept constant, this processed blood sample is only diluted 1:10. If 1 ml of a membrane solubilizing agent comprising 10% of 1-Methyl-1-octyl pyrrolidiniumchloride and 4% of KSCN, respectively, is mixed with 1 ml of whole blood diluted 1:1 in PBS differential hemolysis is also observed. Alternatively 1 ml of whole blood could be added to 2 ml of a membrane solubilizing agent comprising 10% of 1-Methyl-1-octyl pyrrolidiniumchloride and 4% of KSCN, respectively.

For many routine applications it is expected that the ideal ratio of whole blood sample to a membrane solubilizing agent will be between 10:1 and 1:50. Preferably in a method according to the present invention the sample of whole blood is mixed with the hemolysis reagent at a ratio from 5 to 1 to 1 to 20. More preferred the ratio is between 2 to 0.1 and 1 to 10, also preferred between 1 to 1 and 1 to 5. The final, i.e. highest possible concentration of an adjusted hemolysis reagent used in the clinical routine will depend on the solubility and also the price of such reagent.

Preferably an appropriate reagent for different hemolysis is further characterized in that the (minimal) concentration of the chemical required for disrupting the membrane of a red blood cell and the (maximal) concentration tolerated for said chemical at which at the same time no precipitation of sample constituents is caused are at least two-fold apart. The broader the window between minimal and maximal concentration for a the reagent responsibly for differential hemolysis the more easy such reagent can be used in clinical diagnostic routine.

It is further preferred that the membranolytic chemical comprised in a reagent for differential hemolysis is used at a concentration that after mixing said reagent with a sample the final concentration of this membranolytic chemical corresponds to the mean value plus 30% of the minimal concentration minus 30% the maximal concentration, respectively. Further preferred the concentration of the membranolytic chemical comprised in the reagent for differential hemolysis will be adjusted that after mixing it with a sample it is within plus or minus 25%, 20% or 15% of the mean value of the minimal and maximal concentration, respectively.

It is also preferred that the membranolytic chemical comprised in a reagent for differential hemolysis is used at a concentration that after mixing it with a sample it results in a final concentration of this hemolytic chemical corresponding to a concentration between one and four times the minimal concentration, and also preferred between 1.5 times and 3 times the minimal concentration determined as described above.

Preferably the reagent for differential hemolysis in a membrane solubilizing agent of the present invention is used at a concentration of no more than 75% weight/volume, also preferred at no more than 50% weight/volume.

Preferably the method of processing a liquid sample by a membrane solubilizing reagent according to the present invention is followed by an online liquid chromatography (LC) step.

In a further preferred embodiment the present invention relates to a method of detecting an analyte in a liquid sample the method comprising the steps of obtaining said liquid sample, subjecting said liquid sample to a method of sample processing by a membrane solubilizing agent, wherein the solubilizing agent is appropriate to disrupt the membrane of red blood cells, and not to destroy the nuclei of eukaryotic cells, subjecting said processed sample to liquid chromatography and analyzing the analyte under investigation by appropriate means. Preferably the method of analysis is also performed directly (online) upon the processed sample.

Liquid chromatography (LC) is an extremely important analytical technique which is used for the separation, identification and quantification of an analyte of interest even if present in a complex mixture of different sample constituents. During LC the chemical components in a mixture are carried through a stationary phase by the flow of a liquid mobile phase. Separation in liquid chromatography is achieved by means of differences in the interactions of the analytes with both the mobile and stationary phases. As the skilled artisan appreciates both a stationary phase and a mobile phase appropriate to the analytes under investigation have to be chosen. In addition, the user will identify chromatographic conditions appropriate to maintain the sharpness of analytic bands as a sample moves through the stationary phase column to the detector.

High Performance Liquid Chromatography, also known as High Pressure Liquid Chromatography, abbreviated as HPLC, is a special form of liquid chromatography and nowadays used frequently in biochemistry and analytical chemistry. The analyte is forced through a column of the stationary phase in a liquid (mobile phase) at high pressure, which decreases the time the separated components remain on the stationary phase and thus the time they have to diffuse within the column. This leads to narrower peaks in the resulting chromatogram and thence to better resolution and sensitivity as compared to LC.

The mobile phase is chosen to ensure solubility of the sample solutes. For the stationary phase, preferably microparticulate silica (bare or chemically modified) is used, because its high surface area accentuates the differences in solute-stationary phase interactions. The use of a stationary phase that interacts strongly with solutes relative to solute mobile-phase interactions will result in very long retention times, a situation which is not analytically useful. Hence the stationary phase must be selected so as to provide weak to moderate solute interactions relative to those in the mobile phase. As a consequence, the nature of the solute governs the type of LC selected. The stronger interactions should occur in the mobile phase to ensure sample solubility and ready elution, while the stationary phase should be responsive to more subtle differences among the solutes. For example, polar neutral compounds are usually better analyzed using a polar mobile phase together with a nonpolar stationary phase that distinguishes subtle differences in the dispersive character of the solutes. One of the powerful aspects of HPLC is that the mobile phase can be varied to alter the retention mechanism. Modifiers can be added to the mobile phase to control retention. For example, pH is an important variable in aqueous mobile phases.

Five general classes of LC can be distinguished:
1. Normal-phase chromatography calls for the use of a polar stationary phase in conjunction with a non-polar (dispersive) mobile phase.
2. Reversed-phase chromatography, the opposite possibility, calls for the use of a non-polar stationary phase and a polar mobile phase (composed of one or more of the polar solvents, e.g. water, methanol, acetonitrile, and tetrahydrofuran).
3. Ion-exchange chromatography involves ionic interactions. In this case the mobile phase must support ionization to ensure solubility of ionic solutes. The stationary phase must also be partially ionic to promote some retention. Consequently, the interactions with the stationary phase are strong, and this is usually reflected in longer analysis times and broad peaks.
4. Size-Exclusion chromatography involves separations based on molecular size alone and ideally requires that there be no energetic interaction of the solutes with the stationary phase.
5. Affinity chromatography is based on a specific interaction, e.g. between the members of a specific binding pair, like antigen and corresponding antibody or receptor and corresponding ligand. For example a first partner of a binding pair is bound to an appropriate stationary phase and used to capture the second partner of the binding pair. The second partner can be released and isolated by appropriate means.

The general classification of separation principles given above must not be exhaustive and therefore is non-limiting, there are other separation principles which can be used for the separation of liquid samples, e.g. hydrophobic interaction chromatography, hydrophilic interaction chromatography, ion-pair chromatography, and molecular imprinted materials based separation.

In routine applications the stationary phase, the so-called bed material, e.g. silica particles in an RP-HPLC-application, is packed into an appropriate column, and is protected by a frit. The frit material usually is selected to have e.g. a smaller pore size as compared to the pore size of the bed material.

In HPLC methods the diameter of the stationary phase particles usually is in the range of 1 to 10 µm. These small particles necessitate the high pressure used in HPLC. The bed material usually is protected by a frit. Typical frits have a pore size of 1 µm, 0.45 µm or 0.2 µm. The smaller the particles the smaller is usually the pore size of the frit. If a sample comprises a constituent capable of blocking an HPLC frit this is detrimental for any routine analysis. A whole blood sample, as well as an "over-treated" whole blood sample comprising precipitates of sample constituents causes a rapid blocking of any routine HPLC frit or column. As the skilled artisan will appreciate blocking of the frit used in an HPLC column will occur the more rapidly the lower the pore size of the frit, the smaller the diameter of the stationary phase particles and the smaller the column diameter. In case the frit would not be selected appropriately, i.e. a too large pore size, the particle size of the column material would also matter and the column itself would block more rapidly the smaller the particles are.

By applying the treatment with a membrane solubilizing agent according to the present invention to a sample, e.g. to a sample of whole blood it is now possible to directly apply such treated sample to an HPLC column, without running the risk of blocking the column. In a preferred embodiment the present invention relates to a method of processing a liquid sample wherein said sample is first subjected to treatment with a membrane solubilizing agent according to the present invention and is thereafter subjected to an HPLC step. Preferably this HPLC step is performed online with the sample obtained by treatment with a membrane solubilizing agent. Preferably, the stationary phase particles used in such HPLC step are in the range of 1 to 10 µm, also preferred in the range of 2 to 7 µm in diameter. Preferably the frit used in such HPLC step has a pore size of 0.5 µm or also preferred of 0.2 µm.

The analyte of interest can be detected by any appropriate means. Appropriate and preferred detectors sense the presence of a compound passing through, and provide an electronic signal to a recorder or computer data station. The output is usually in the form of a chromatogram and a substance of interest is usually found in a certain peak. The peak area or peak height can be used to quantify the amount of analyte present in the sample investigated.

The detector for an HPLC system is the component that emits a response due to the eluting sample compound and subsequently signals a peak on the chromatogram. It is positioned immediately posterior to the stationary phase in order to detect the compounds as they elute from the column. The bandwidth and height of the peaks may usually be adjusted using the coarse and fine tuning controls, and the detection and sensitivity parameters may also be controlled by the skilled artisan. There are many types of detectors that can be used with HPLC. Some of the more common detectors include: Refractive Index (RI), Ultra-Violet (UV), Fluorescent, Radiochemical, Electrochemical, Near-Infra Red (Near-IR), Mass Spectroscopy (MS), Nuclear Magnetic Resonance (NMR), and Light Scattering (LS).

Refractive Index (RI) detectors measure the ability of sample molecules to bend or refract light. This property for each molecule or compound is called its refractive index. For most RI detectors, light proceeds through a bi-modular flow-cell to a photodetector. One channel of the flow-cell directs the mobile phase passing through the column while the other directs only the mobile phase. Detection occurs when the light is bent due to samples eluting from the column, and this is read as a disparity between the two channels.

Fluorescent detectors measure the ability of a compound to absorb then re-emit light at given wavelengths. Each compound has a characteristic fluorescence. The excitation source passes through the flow-cell to a photodetector while a monochromator measures the emission wavelengths.

Radiochemical detection involves the use of radiolabeled material, usually tritium (3H) or carbon-14 (14C). It operates by detection of fluorescence associated with beta-particle ionization, and it is most popular in metabolite research.

Electrochemical detectors measure compounds that undergo oxidation or reduction reactions. This is usually accomplished by measuring gain or loss of electrons from migrating samples as they pass between electrodes at a given difference in electrical potential.

Mass spectrometry is an analytical technique used to measure the mass-to-charge ratio (m/z (or m/q)) of ions. It is most generally used to analyze the composition of a physical sample by generating a mass spectrum representing the masses of sample components. The technique has several applications, including: identifying unknown compounds by the mass of the compound and/or fragments thereof; determining the isotopic composition of one or more elements in a compound; determining the structure of compounds by observing the fragmentation of the compound; quantitating the amount of a compound in a sample using carefully designed methods (mass spectrometry is not inherently quantitative); studying the fundamentals of gas phase ion chemistry (the chemistry of ions and neutrals in vacuum); determining other physical, chemical or even biological properties of compounds with a variety of other approaches.

A mass spectrometer is a device used for mass spectrometry, and produces a mass spectrum of a sample to analyze its composition. This is normally achieved by ionizing the sample and separating ions of differing masses and recording their relative abundance by measuring intensities of ion flux. A typical mass spectrometer comprises three parts: an ion source, a mass analyzer, and a detector.

The kind of ion source is a contributing factor that strongly influences what types of samples can be analyzed by mass spectrometry. Electron ionization and chemical ionization are used for gases and vapors. In chemical ionization sources, the analyte is ionized by chemical ion-molecule, reactions during collisions in the source. Two techniques often used with liquid and solid biological samples include electrospray ionization (ESI) and matrix-assisted laser desorption/ionization (MALDI), Other techniques include fast atom bombardment (FAB), thermospray, atmospheric pressure chemical ionization (APCI), secondary ion mass spectrometry (SIMS) and thermal ionization.

In a preferred embodiment the detecting of an analyte in a method according to the present invention is performed by mass spectroscopy.

Nuclear magnetic resonance (NMR) detection is based on the fact that certain nuclei with odd-numbered masses, including H and $^{13}$C, spin about an axis in, a random fashion. However, when placed between poles of a strong magnet, the spins are aligned either parallel or anti-parallel to the magnetic field, with the parallel orientation favored since it is slightly lower in energy. The nuclei are then irradiated with electromagnetic radiation which is absorbed and places the parallel nuclei into a higher energy state; consequently, they are now in "resonance" with the radiation. Each H or C will produce different spectra depending on their location and adjacent molecules, or elements in the compound, because all nuclei in molecules are surrounded by electron clouds which change the encompassing magnetic field and thereby alter the absorption frequency.

When a source emits a parallel beam of light which strikes particles in solution, some light is reflected, absorbed, transmitted, or scattered. These phenomena can be measured by a light-scattering (LS) detector. The most prominent forms of LS detection are termed nephelometry and turbidometry. Nephelometry is defined as the measurement of light scattered by a particulate solution. This method enables the detection of the portion of light scattered at a multitude of angles. Turbidometry is defined as the measure of the reduction of light transmitted due to particles in solution. It measures the light scatter as a decrease in the light that is transmitted through the particulate solution. Therefore, it quantifies the residual light transmitted.

Near-infrared detectors operate by scanning compounds in a spectrum from 700 to 1100 nm. Stretching and bending vibrations of particular chemical bonds in each molecule are detected at certain wavelengths.

In a preferred embodiment according to the present invention a whole blood sample derived from a mammal or a sample of anti-coagulated whole blood derived from a mammal will be subjected to the treatment with a membrane solubilizing agent as described in the present invention and the analyte of interest comprised in the such treated sample will be detected online, i.e. without any additional step like filtration, precipitation or centrifugation. In a preferred embodiment the present invention therefore relates to method of analyzing a sample of whole blood, comprising the steps of processing the sample with a membrane solubilizing agent under conditions appropriate to disrupt the membrane of said red blood cells and not to destroy the nuclei of eukaryotic cells, subjecting said processed sample to an HPLC step and detecting an analyte of interest in said sample. Preferably the three steps in the above analysis are performed online.

An analyte according to the present invention may be any inorganic or organic molecule, including a biomolecule, excluding nucleic acids. The analyte will not be a nucleic acid, especially it will not be a DNA. Preferably the analyte is selected from the group consisting of a polypeptide, a carbohydrate, and an inorganic or organic drug molecule. Preferably the analyte of interest has an MW of 10,000 Da or less, also preferred of 9 kDa or less, of 8 or less, of 7 kDa or less, of 6 kDa or less, or of 5 kDa or less, respectively.

A polypeptide or protein is a molecule that is essentially composed of amino acids and that has at least two amino acids linked by peptidic linkage. In case the analyte of interest to be investigated in a method disclosed here, the polypeptide preferably will consist of at least 3, 4, 5, 6, 7, 8, 9, 10, 12, 15, 20, 25, and 30 to up to about 100 amino acids. Preferably the polypeptide will contain from 5 to 100, also preferred from 10 to 40 amino acids. Suitable peptidic analytes of interest are e.g. peptide hormones, and other polypeptides present in the circulation and especially polypeptides released from red blood cells due to the treatment with a membrane solubilizing agent according to the present invention.

Preferably the method according to the present invention is used in the online detection of an analyte from a whole blood sample wherein said analyte is at least partially located inside a red blood cell.

A preferred target analyte according to the present invention is selected from the group consisting of the drugs of abuse and the immunosuppressive drugs.

Preferred target analytes are the drugs of abuse. The drug of abuse is preferably selected from the group consisting of amphetamine, cocaine and cocaine metabolites like benzoylecgnonine, methamphetamine, opiate and opiate derivatives, cannabinoids like tetrahydrocannabinol, and phencyclidine.

A further preferred target analyte is folate especially the total folate as comprised in both the blood plasma and in the red blood cells.

Preferred target analytes are immunosuppressive drugs. The immunosuppressive drug is preferably selected from the group consisting of cyclosporine (CsA), mycophenolate mofetil (MMF), rapamycin (RAPA also known as sirolimus), tacrolimus (FK-506) azathioprine (AZA), and methylprednisolone (MP).

Also preferred is a target analyte that is present in a red blood cell. Preferred analytes to be measured from a differentially hemolyzed whole blood sample are sirolimus, tacrolimus and folate.

The following examples and figures are provided to aid the understanding of the present invention, the true scope of which is set forth in the appended claims. It is understood that modifications can be made in the procedures set forth without departing from the spirit of the invention.

Example 1

Evaluation of Various Candidate Hemolysis Reagents

Example 1.1

Visual Evaluation of Hemolysis

Solution A: Fresh EDTA-stabilized whole blood is diluted with 0.15 molar sodium chloride solution in the ratio 1:10 (50 µL EDTA-blood plus 450 µL sodium chloride solution).

Solution B: A solution of the candidate hemolysis reagent in 0.15 molar sodium chloride is prepared wherein the concentration of the hemolysis reagent is twice as high as the desired final concentration in the hemolysate, e.g. to get a final concentration of 25% of 1-Butyl-4-methylpyridinium tetrafluoroborate a solution of 50% (50 mg salt plus 50 mL 0.1.5 molar sodium chloride in water) is prepared.

In the case of the addition of a second compound, e.g. potassium iodide (1-Butyl-3-methyl pyridiniumchloride/KJ) the stated salt is added in an approximately equimolar amount.

Hemolysate is prepared by mixing solution A and B in equal volumes, e.g. 500 µL solution A plus 500 µL solution B.

After mixing the hemolysate is inspected visually for turbidometry and clearness immediately after mixing, after 1 minute, 2, 5, 6, 7, 20 and 40 minutes. The time until a clear solution is observed is recorded.

TABLE 1

Visual evaluation of candidate reagents for differential hemolysis

| Hemolysis reagent | final concentration (weight/volume) | clear after (min.) |
|---|---|---|
| 1-Butyl-4-methylpyridinium tetrafluoroborate | 25% | 20 min. |
| 1-Butyl-4-methylpyridinium tetrafluoroborate | 12.5% | 40 min. |
| 1-Butyl-4-methylpyridinium tetrafluoroborate | 6% | turbid |
| 1-Butyl-3-methyl-imidazolium tetrafluoroborate | 25% | 20 min. |
| 1-Butyl-3-methyl-imidazoliumoctylsulfate | 25% | immediately |
| 1-Butyl-3-methyl pyridiniumchloride | 25% | turbid |
| 1-Butyl-3-methyl pyridiniumchloride/KJ | 25%/22% | 20 min. |
| 1-Butyl-3-methyl pyridiniumchloride/KSCN | 25%/13% | 5 min. |
| 1-Hexylpyridiniumchloride/KSCN | 25%/12% | immediately |
| 1-Hexylpyridiniumchloride/KSCN | 12.5%/6% | 1 min. |
| 1-Hexylpyridiniumchloride/KSCN | 6.25%/3% | 6 min. |
| 1-Hexylpyridiniumchloride/KSCN | 3.12%/1.5% | turbid |
| 1-Hexylpyridiniumchloride | 25% | 7 min. |
| 1-Hexylpyridiniumchloride | 12.5% | turbid |
| 1-Methyl-1-octyl pyrrolidiniumchloride/KSCN | 25%/10% | immediately |
| 1-Methyl-1-octyl pyrrolidiniumchloride/KSCN | 12.5%/5% | immediately |

TABLE 1-continued

Visual evaluation of candidate reagents for differential hemolysis

| Hemolysis reagent | final concentration (weight/volume) | clear after (min.) |
|---|---|---|
| 1-Methyl-1-octyl pyrrolidiniumchloride/KSCN | 6.25%/2.5% | immediately |
| 1-Methyl-1-octyl pyrrolidiniumchloride/KSCN | 3.12%/1.25% | immediately |
| 1-Methyl-1-octyl pyrrolidiniumchloride/KSCN | 2.5%/1% | immediately |
| 1-Methyl-1-octyl pyrrolidiniumchloride/KSCN | 1.25%/0.5% | 2 min. |
| 1-Methyl-1-octyl pyrrolidiniumchloride/KSCN | 0.62%/0.25% | turbid |
| 1-Methyl-1-octyl pyrrolidiniumchloride | 25% | immediately |
| 1-Methyl-1-octyl pyrrolidiniumchloride | 2.5% | turbid |
| N-Octylpyridiniumchloride | 25% | 2 min. |
| 3-Carbamoyl-1-octyloxymethyl pyridiniumchloride | 12.5% | immediately |
| 3-Carbamoyl-1-octyloxymethyl pyridiniumchloride | 6.25% | immediately |
| 3-Carbamoyl-1-octyloxymethyl pyridiniumchloride | 1.5% | immediately |

As is obvious from the above table, by visual assessment good candidate reagents for differential hemolysis can be identified visually.

Example 1.2

Microscopic Evaluation of Hemolysis

Solution A: Fresh EDTA-stabilized whole blood is diluted with 0.15 molar sodium chloride solution in the ratio 1:10 (50 µL EDTA-blood plus 450 µL sodium chloride solution).

Solution B: A solution of the hemolysis reagent in 0.15 molar sodium chloride is prepared where the concentration of the hemolysis reagent is twice as high as the desired final concentration in the hemolysate, e.g. to get a final concentration of 25% of 1-Butyl-4-methylpyridinium tetrafluoroborate a solution of 50% (50 mg salt plus 50 mL 0.15 molar sodium chloride in water) is prepared. In the case of the addition of a second anion, e.g. iodide (1-Butyl-3-methylpyridiniumchloride/KJ) the stated salt is added in an equimolar amount.

Hemolysate is prepared by mixing solution A and B in equal volumes, e.g. 20 µL solution A plus 20 µL solution B. May-GrüNwald Staining and Microscopy:

After mixing of the hemolysate a droplet is smeared on a microscope slide, air dried at room temperature and stained with May-Grünwald staining reagent (Merck Cat. No. 1.01424 May-Grünwald's Eosin Methylene Blue Solution). After May-Grünwald-staining nuclei stain to varying shades of purple, cytoplasm is seen in tones of blue to light pink, fine reddish to lilac granules may be present in cytoplasm of some cell types, basophiles will demonstrate dark blue black granules in the cytoplasm, eosinophils will demonstrate bright orange granules in the cytoplasm, and red blood cells are stained pink to orange.

Microscopy is performed by oil immersion light microscopy (magnification ×630).

Figure 1:
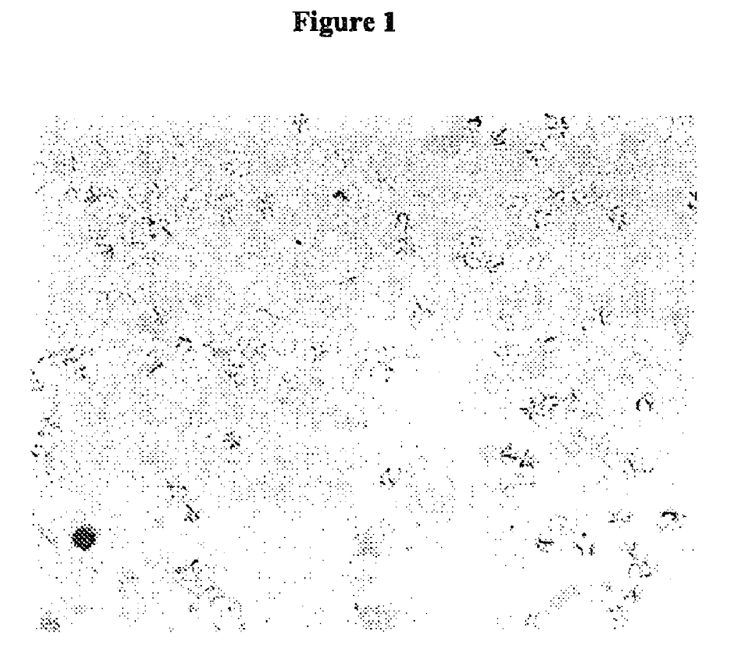
FIG. 1: Light microscopy of a 1 in 10 diluted whole blood hemolyzed with water. May-Grünwald staining has been applied. Erythrocyte membranes and nuclei are visible.
Figure 2:
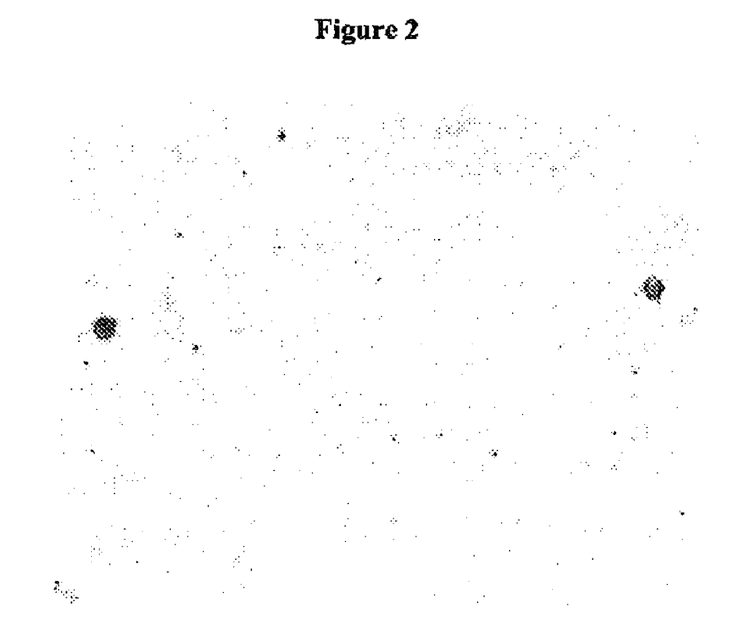
FIG. 2: Light microscopy of a 1 in 10 diluted whole blood hemolyzed with 1-Butyl-4-methylpyridinium tetrafluoroborate (25%). May-Grünwald staining has been applied. No erythrocytes or membranes are left, nuclei are still intact.

Comparative results—FIG. 1 lysate obtained by water and FIG. 2 lysate obtained according to the present invention, respectively—show that the addition of an appropriate hemolyzing reagent within a few minutes will lead to complete lysis of erythrocytes.

Trypane Blue Staining and Microscopy:

The processed whole blood sample is mixed (1:1) with Trypane blue solution (Merck cat. no. 1.11732; Trypanblau C.I. 23850) and dispensed into a Neugebauer-chamber for microscopy. Microscopy is performed by oil immersion light microscopy (magnification ×630).

Figure 3:
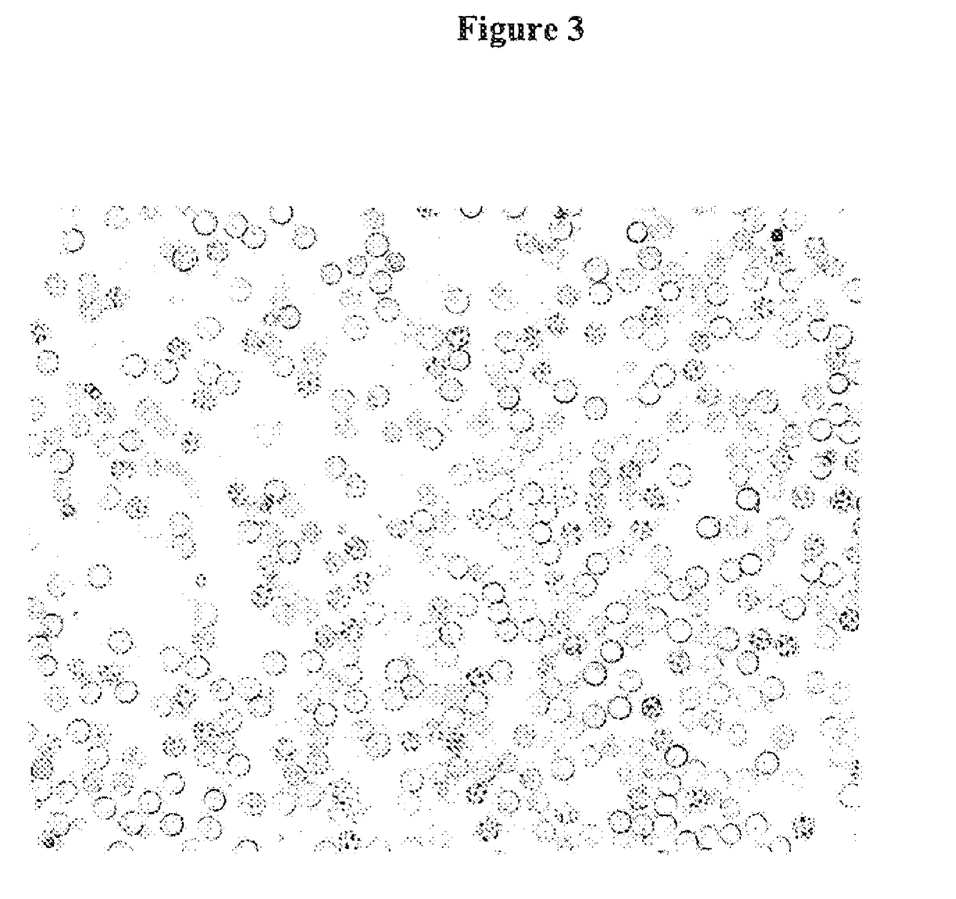
FIG. 3: Light microscopy of a 1 in 10 diluted whole blood hemolyzed with water. Trypane blue staining has been used.
Figure 4A:
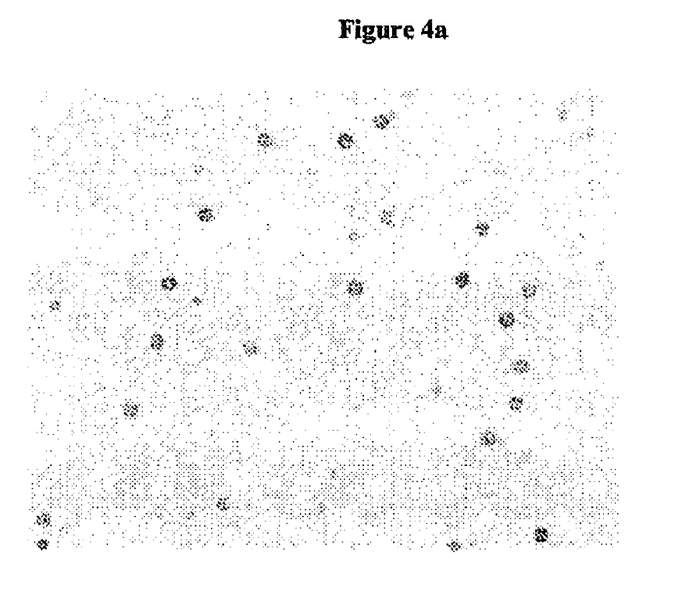
FIG. 4: Light microscopy of a 1 in 10 diluted whole blood hemolyzed with 1-Butyl-4-methylpyridinium tetrafluoroborate (25%). Trypane blue staining has been used. a) 2.5 min incubation time: Only few residual erythrocytes are left b) 15 min incubation time: No erythrocytes or membranes are left.
Figure 4B:
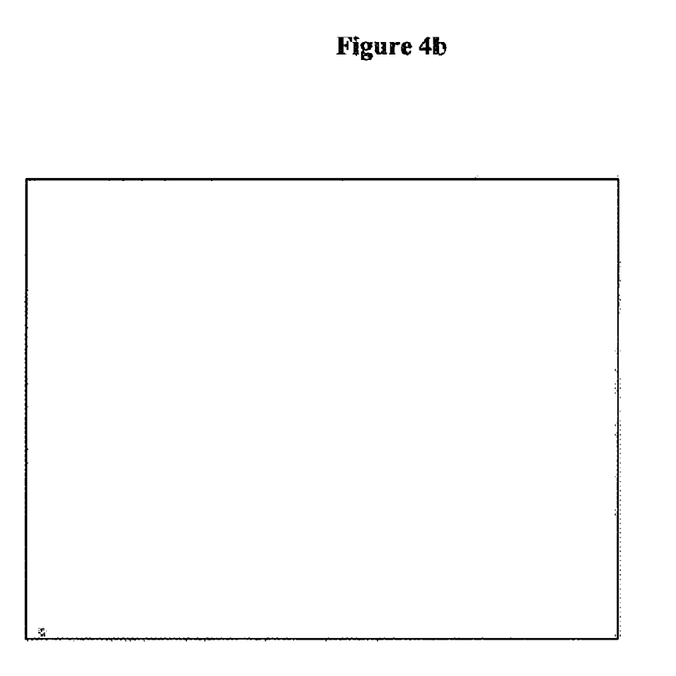

Comparative results—FIG. 3 lysate obtained by water and FIGS. 4a) and b) lysates obtained according to the present invention, respectively—show that the addition of an appropriate hemolyzing reagent within a few minutes will lead to complete lysis of erythrocytes.

Example 2

Evaluation of Various Candidate Hemolysis Reagents by HPLC

To assess lysis efficiency a hemolyzed whole blood sample prepared according example 1 is injected into a HPLC system and the backpressure of the system is monitored.

The HPLC system consists of an HP 1090 liquid chromatograph (Agilent) with a DR 5 solvent delivery system, a thermostat equipped auto sampler and an auto injector. Lysis efficacy is assessed by applying 50 times 10 μL of the treated whole blood sample to an HPLC column having 5 μm Symmetry C18 particles as bed material, an inner column diameter of 2 mm, column length of 20 mm and a frit with 0.5 μm pore size. The eluent is a gradient from water with 0.1% formic acid to acetonitrile with 0.1% formic acid within 5 minutes and at a flow rate of 0.2 mL/min. The observed increase of back pressure over 50 injections is less than 20 bar.

If lysis is achieved with distilled water only, the observed increase of back pressure under the above HPLC conditions is more than 100 bar.

Example 3

Measurement of Rapamycin from a Sample of Whole Blood

A whole blood sample is spiked with rapamycin, and mixed with hemolyzing reagent. 50 μL of a solution of 400 μg/mL rapamycin in 50% methanol/water is added to 450 μL fresh EDTA-blood, homogenized and incubated for 1 hour at room temperature.

A 50 μL aliquot of this spiked whole blood sample is diluted with 950 μL of a 25% solution of 1-Butyl-4-methylpyridinium tetrafluoroborate in 0.15 molar sodium chloride water. 25 μL of the hemolysate are injected into the HPLC.

Figure 5:
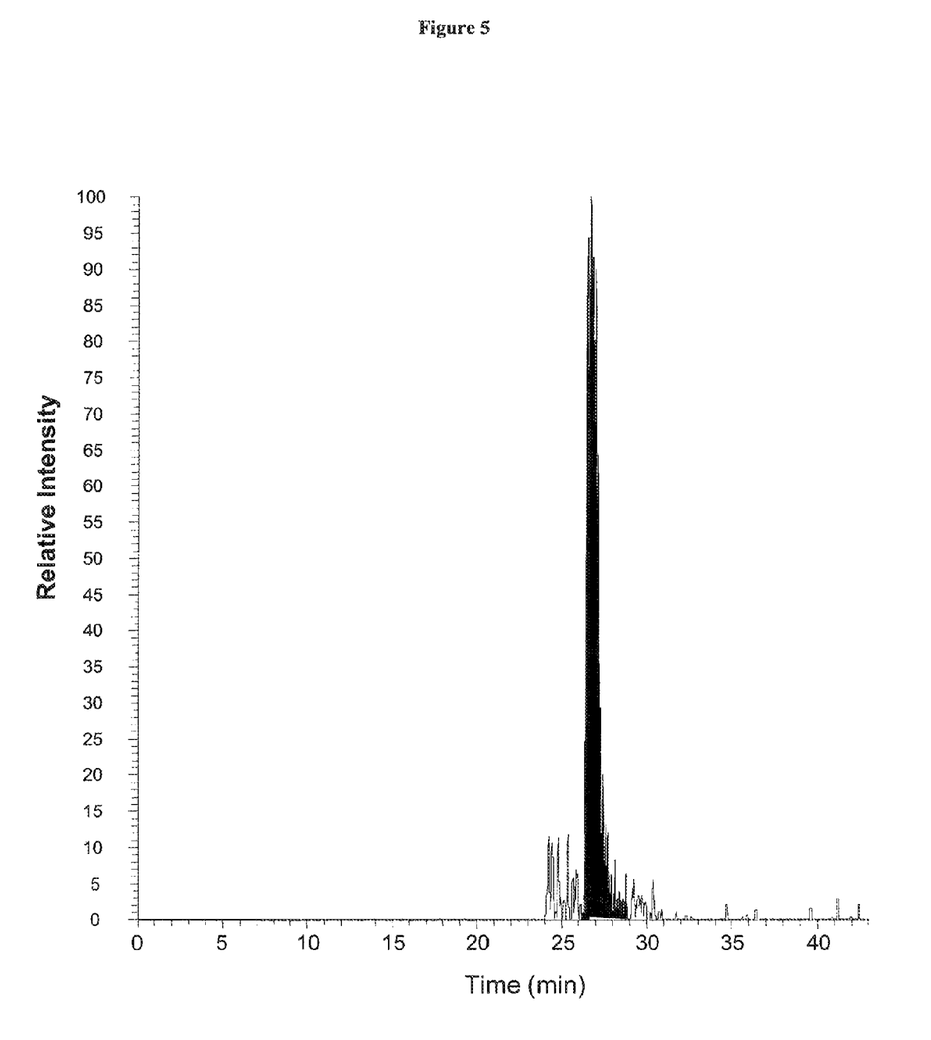
FIG. 5: LC-MS/MS chromatogram of a 1 in 10 diluted whole blood spiked with rapamycin.

The HPLC system consists of an HP 1090 liquid chromatograph (Agilent) with an DR 5 solvent delivery system, a thermostat equipped auto sampler, an auto injector and a diverte valve between HPLC and mass spectrometer. Detector is a linear ion trap mass spectrometer, Thermo Electron LTQ, with electrospray ionization. For chromatographic separation a HPLC column having 5 μm Vydac C18 particles as bed material, an inner column diameter of 2 mm, column length of 250 mm and a frit with 0.5 μm pore size is used. The eluent is a gradient from water with 0.1% formic acid (A) to acetonitrile with 0.1% formic acid (B) within 30 minutes and thereafter is isocratic for 10 min at 100% B. The flow rate is 0.2 mL/min. Rapamycin elutes at approximately 26 minutes (cf. FIG. 5).

Example 4

Measurement of 5-Methyl Tetrahydrofolate from a Sample of Whole Blood

A whole blood sample is spiked with 5-methyl tetrahydrofolate, and mixed with hemolyzing reagent, 10 μL of a solution of 10 μg/mL 5-methyl tetrahydrofolate in water with 1% ascorbic acid (adjusted to pH 7 with 4 M sodium hydroxide solution) is added to 90 μL fresh EDTA-blood. 10 μL of this spiked blood is diluted with 90 μL 0.15 molar sodium chloride in water and mixed with 100 μL of a solution of 2 mg 1-Methyl-1-octyl pyrrolidiniumchloride/KSCN in 1% ascorbic acid (adjusted to pH 7 with 4 M sodium hydroxide solution). This hemolysate is used for HPLC analysis.

The HPLC system consists of an HP 1090 liquid chromatograph (Agilent) with an DR 5 solvent delivery system, a thermostat equipped auto sampler, an auto injector and a 6 port diverte valve for column switching between precolumn and analytical HPLC column. For injection and loading of the precolumn a Waters HPLC 515 pump is used. Detector is a linear inontrap mass spectrometer, Thermo Electron LTQ, with electrospray ionization. For chromatographic separation a precolumn ADS-C18, 25×4 mm (Merck) and an analytical HPLC column having 5 μm Vydac C18 particles as bed material, an inner column diameter of 2.1 mm, column length of 250 mm and a frit with 0.5 μm pore size is used. Solvent A is water with 0.5% acetic acid, solvent B is methanol with 0.5% acetic acid.

Figure 6:
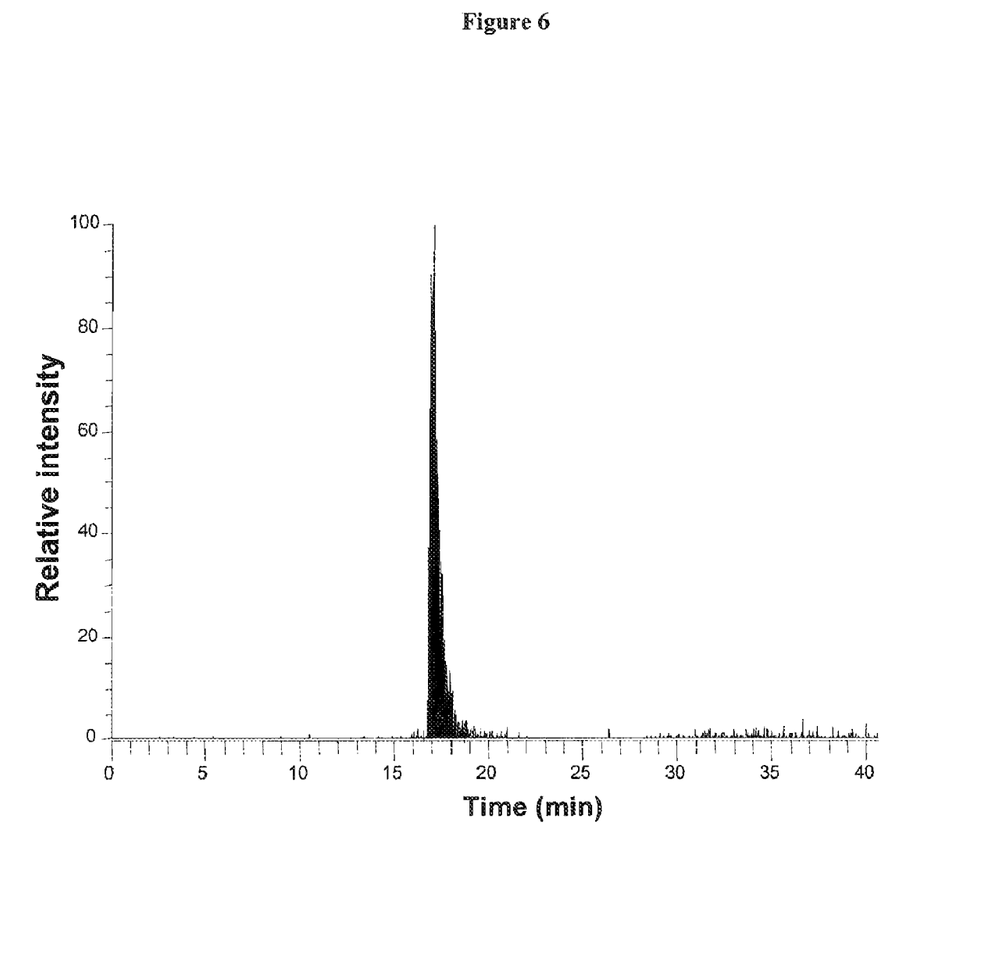
FIG. 6: LC-MS/MS chromatogram of a whole blood spiked with 5-methyl tetrahydrofolate. 5-methyl tetrahydrofolate elutes at 17.5 minutes.

Of the spiked and hemolyzed sample 20 μL are injected onto the precolumn ADS-C18 with eluent A at a flow rate of 1.5 mL/min. After 4 minutes the trapped analyte is eluted in backflush mode with a flow rate of 0.2 mL/min onto the analytical column Vydac C18 by applying a gradient from water (with 0.5% acetic acid) (A) to methanol (with 0.5% acetic acid) (B) using 0% B until 5 minutes, and a gradient to 100% B between 5 and 30 minutes at a flow rate of 0.2 mL/min. The analyte 5-methyl tetrahydrofolate elutes at approximately 17 minutes (cf. FIG. 6).

What is claimed is:

1. A method for detecting an analyte in a liquid biological sample known or suspected to comprise red blood cells and suspected or known to comprise eukaryotic cells, the method comprising the steps of (a) processing said liquid sample with a membrane solubilizing agent thereby lysing cell membranes of red blood cells without releasing nucleic acid and without causing precipitation of sample constituents, (b) subjecting the processed sample obtained in step (a) to a chromatographic separation, wherein said chromatographic separation is by high performance liquid chromatography (HPLC) and (c) detecting the analyte, (d) wherein said analyte is at least partially located inside a red blood cell and wherein the membrane solubilizing agent comprises a chemical selected from the group consisting of KBr, KJ, KSCN, and a salt consisting of a cation selected from the group consisting of wherein m is 0 or 1 and n is 4 or 6, and wherein the anion is selected from the group consisting of chloride, tetrafluoroborate, octylsulfate, iodide, and thiocyanate.

2. The method of claim 1, wherein said chromatographic separation is based on column chromatography and performed by use of a column comprising a frit and a bed material or by use of a monolithic column.

3. The method of according to claim 2, wherein said frit has a pore size of 0.2 or 0.5 µm.

4. The method according claim 2, wherein said bed material is particulate and the particles have a diameter from 1 to 10 µm.

5. The method of claim 1, wherein said analyte is detected by mass spectroscopy.

6. The method of claim 1, wherein said biological sample is selected from cerebrospinal fluid and whole blood.

7. The method according to claim 1, wherein said analyte is an immunosuppressive drug.

* * * * *